(12) United States Patent
Adams et al.

(10) Patent No.: US 11,322,239 B2
(45) Date of Patent: May 3, 2022

(54) MEDICAL DEVICE DISPOSABLES INFORMATION SYSTEMS AND METHODS

(71) Applicant: Smiths Medical ASD, Inc., Plymouth, MN (US)

(72) Inventors: Grant A. Adams, Anoka, MN (US); Alison L. Bloomquist, Gem Lake, MN (US); Ryan D. Heilman, Columbia Heights, MN (US); Michael D. Welsch, Stillwater, MN (US); Larry R. Zalesky, Shoreview, MN (US)

(73) Assignee: Smiths Medical ASD, Inc., Plymouth, MN (US)

( * ) Notice: Subject to any disclaimer, the term of this patent is extended or adjusted under 35 U.S.C. 154(b) by 801 days.

(21) Appl. No.: 15/775,292

(22) PCT Filed: Dec. 1, 2016

(86) PCT No.: PCT/US2016/064319
§ 371 (c)(1),
(2) Date: May 10, 2018

(87) PCT Pub. No.: WO2017/095982
PCT Pub. Date: Jun. 8, 2017

(65) Prior Publication Data
US 2018/0353678 A1  Dec. 13, 2018

Related U.S. Application Data

(60) Provisional application No. 62/262,112, filed on Dec. 2, 2015.

(51) Int. Cl.
*G16H 20/17* (2018.01)
*A61M 5/142* (2006.01)
*A61M 5/168* (2006.01)

(52) U.S. Cl.
CPC ............ *G16H 20/17* (2018.01); *A61M 5/142* (2013.01); *A61M 5/14228* (2013.01);
(Continued)

(58) Field of Classification Search
CPC ......... A61M 2005/14268; A61M 2005/16863; A61M 2205/12; A61M 2205/3569;
(Continued)

(56) References Cited

U.S. PATENT DOCUMENTS 4,559,038 A  12/1985  Berg et al.
6,744,350 B2  6/2004  Blomquist
(Continued)

FOREIGN PATENT DOCUMENTS

WO  WO 2014/210465 A1  12/2014
WO  WO 2016/018552 A1  2/2016
(Continued)

OTHER PUBLICATIONS

International Search Report for corresponding International Application No. PCT/US2016/064319 dated Mar. 17, 2017; 3 pages.
(Continued)

*Primary Examiner* — Brandy S Lee
(74) *Attorney, Agent, or Firm* — Patterson Thuente Pedersen, P.A.

(57) ABSTRACT

A method for managing use of a disposable with an infusion pump is provided. The method can include adding validity information about a particular set of disposables to a list of disposables. Subsequent to adding the validity information, the method can include modifying the validity information about the particular set of disposables on the list of disposables. The method can include an infusion pump reading identifying information from a disposable, and can include determining whether the disposable is valid for use, based at least in part upon comparison of the identifying information
(Continued)

read from the disposable by the infusion pump with the validity information about the particular set of disposables on the list of disposables. The method can also include the infusion pump making a determination of whether to deliver or not deliver an infusate based at least in part upon the determining whether the disposable is valid for use.

19 Claims, 6 Drawing Sheets

(52) U.S. Cl.
CPC .............. *A61M 5/14244* (2013.01); *A61M 2005/14268* (2013.01); *A61M 2005/16863* (2013.01); *A61M 2205/12* (2013.01); *A61M 2205/3569* (2013.01); *A61M 2205/505* (2013.01); *A61M 2205/52* (2013.01); *A61M 2205/6018* (2013.01); *A61M 2205/6072* (2013.01)

(58) Field of Classification Search
CPC ........ A61M 2205/505; A61M 2205/52; A61M 2205/6018; A61M 2205/6072; A61M 5/142; A61M 5/14228; A61M 5/14244; G16H 20/17
See application file for complete search history.

(56) References Cited

U.S. PATENT DOCUMENTS

| | | |
|---|---|---|
| 7,762,989 B2 | 7/2010 | Simpson |
| 2006/0030049 A1 | 2/2006 | Bhimani et al. |
| 2010/0156633 A1 | 6/2010 | Buck, Jr. et al. |
| 2011/0009724 A1 | 1/2011 | Hill et al. |
| 2011/0118694 A1* | 5/2011 | Yodfat .................. G16H 20/13 604/500 |
| 2011/0152756 A1 | 6/2011 | Drew |
| 2011/0315611 A1* | 12/2011 | Fulkerson .......... A61M 1/3639 210/96.2 |
| 2013/0253430 A1 | 9/2013 | Kouyoumjian et al. |
| 2015/0196709 A1 | 7/2015 | Jacobson et al. |

FOREIGN PATENT DOCUMENTS

| | | |
|---|---|---|
| WO | WO 2016/105899 A1 | 6/2016 |
| WO | WO 2016/160320 A1 | 10/2016 |
| WO | WO 2016/186955 A1 | 11/2016 |

OTHER PUBLICATIONS

Written Opinion of the International Searching Authority for corresponding International Application No. PCT/US2016/064319 dated Mar. 17, 2017; 8 pages.

\* cited by examiner

Method 500

510

Add validity information to list of disposables

520

Modify validity information

530

Read identifying information from disposable

540

Determine whether disposable is valid for use based upon comparison of identifying information with validity information

550

Determine whether to use disposable based upon whether disposable is determined to be valid for use

FIG. 5

Method 600

610

Obtain information about attached disposable

620

Self-program to prime based on obtained information

630

Deliver infusate to prime based on self-programming

*FIG. 6*

MEDICAL DEVICE DISPOSABLES INFORMATION SYSTEMS AND METHODS

CROSS-REFERENCE TO RELATED APPLICATIONS

The present application is a National Phase entry of PCT Application No. PCT/US2016/064319, filed on Dec. 1, 2016, which claims priority to U.S. Provisional Patent Application No. 62/262,112, filed on Dec. 2, 2015, which are hereby fully incorporated herein by reference.

TECHNICAL FIELD

This disclosure relates to medical devices, and more particularly, to medical devices with disposable components.

BACKGROUND

A variety of medical devices are known in which a main unit can be operated in combination with one or more disposable elements during each use of the device. For example, a convective patient warming system can include a main heater/blower unit that is coupled to disposable warming blankets. In another example, a patient monitoring device can include a main unit that attaches to one or more disposable sensors, such as electrodes. In yet other examples, infusion pump systems can include a main pump unit that couples to an infusate reservoir (such as an IV bag or reservoir cassette), one or more infusion lines, and/or possibly other disposable components. As used throughout this document, the term "disposable" is intended to include any such disposable element for use with a medical device.

In some examples, a plurality of different types of disposables, or combinations of disposables, can be used with a particular main unit. In many medical devices used with disposables, the main unit has little or no ability to acquire, recognize, or use information concerning the disposable(s) with which it operates. For improved functionality and safety, it would be desirable to provide systems and methods that allow medical devices to exploit information about disposables with which they operate.

SUMMARY

This disclosure relates to medical devices, and more particularly, to medical devices with disposable components.

In an illustrative but non-limiting example, the disclosure provides a method for managing use of a disposable with an infusion pump. The method can include adding validity information about a particular set of disposables to a list of disposables. Subsequent to adding the validity information, the method can include modifying the validity information about the particular set of disposables on the list of disposables. The method can include an infusion pump reading identifying information from a disposable, and can include determining whether the disposable is valid for use, based at least in part upon comparison of the identifying information read from the disposable by the infusion pump with the validity information about the particular set of disposables on the list of disposables. The method can also include the infusion pump making a determination of whether to deliver or not deliver an infusate based at least in part upon the determining whether the disposable is valid for use.

In some cases, the method can include, if the disposable is determined to be not valid for use, allowing a user to specify use of the disposable despite the determination that the disposable is not valid for use, and the infusion pump delivering the infusate if the user specifies use of the disposable. In some cases, the infusion pump can notify a user that the disposable has been determined to be not valid for use. Such notification can include a specific reason that the disposable has been determined to be not valid for use.

In some cases, the method can include the infusion pump modifying at least one operating parameter based at least in part the identifying information read from the disposable by the infusion pump. In some such cases, the at least one operating parameter can relate to occlusion detection.

In some cases, the method can include the infusion pump self-programming to deliver infusate sufficient to prime the disposable, with the self-programming based at least in part upon the identifying information read from the disposable by the infusion pump, and then the infusion pump can deliver infusate sufficient to prime the disposable, based upon the self-programming.

In another illustrative but non-limiting example, the disclosure provides another method for managing use of a disposable with an infusion pump. The method can include adding validity information about a particular set of disposables to a list of disposables and an infusion pump reading identifying information from a disposable that is one of the particular set of disposables. The method can include determining that the disposable is not valid for use, based at least in part upon comparison of the identifying information read from the disposable by the infusion pump with the validity information about the particular set of disposables on the list of disposables, and can include the infusion pump notifying a user that the disposable has been determined to be not valid for use. The method can include allowing the user to specify use of the disposable despite the determination that the disposable is not valid for use, and can include the infusion pump delivering the infusate if the user specifies use of the disposable.

In some cases, the method can include, subsequent to adding the validity information, modifying the validity information about the particular set of disposables on the list of disposables.

In some cases, notifying the user that the disposable has been determined to be not valid for use can include notifying the user of a specific reason that the disposable has been determined to be not valid for use.

In some cases, the method can include the infusion pump modifying at least one operating parameter based at least in part the identifying information read from the disposable by the infusion pump. In some such cases, the at least one operating parameter can relate to occlusion detection.

In some cases, the method can include the infusion pump self-programming to deliver infusate sufficient to prime the disposable, with the self-programming based at least in part upon the identifying information read from the disposable by the infusion pump, and then the infusion pump can deliver infusate sufficient to prime the disposable, based upon the self-programming.

In yet another illustrative but non-limiting example, the disclosure provides yet another method for managing use of a disposable with an infusion pump. The method can include an infusion pump obtaining identifying information about an attached disposable, the infusion pump self-programming to deliver infusate sufficient to prime the disposable (the self-programming based at least in part upon the identifying information), and the infusion pump delivering infusate sufficient to prime the disposable, based upon the self-programming. In some cases, obtaining identifying information can include receiving user input via a user interface of the infusion pump. In some cases, obtaining identifying information can include a reader of the infusion pump reading a tag of the disposable.

In still another illustrative but non-limiting example, the disclosure provides a method for managing use of a plurality of disposables with a corresponding plurality of infusion pumps. The method can include each of the plurality of infusion pumps obtaining identifying information about an attached disposable. The method can include providing an infusion planning system for coordination of medical care including management of the plurality of infusion pumps. The method can include inputting identifying information, of the disposables being used for planned therapies for several patients concurrently, to the infusion planning system, and the method can include transmitting such identifying information to a pharmacy for demand planning and physician order forecasting as changes in previously planned patient therapies occur.

The above summary is not intended to describe each and every example or every implementation of the disclosure. The Description that follows more particularly exemplifies various illustrative embodiments.

BRIEF DESCRIPTION OF THE FIGURES

The following description should be read with reference to the drawings. The drawings, which are not necessarily to scale, depict examples and are not intended to limit the scope of the disclosure. The disclosure may be more completely understood in consideration of the following description with respect to various examples in connection with the accompanying drawings, in which.

DESCRIPTION

The present application is related to International Patent Application No. PCT/US2015/038309, titled "MEDICAMENT INFUSION SYSTEM AND PUMP ASSEMBLY FOR USE THEREIN," U.S. Provisional Patent Application Ser. No. 62/139,289, titled "MEDICAL DEVICE CONTROL," International Patent Application No. PCT/US2014/044586, titled "INFUSION PLANNING SYSTEM," and U.S. Provisional Patent Application No. 62/095,522, titled "INFUSION PLANNING SYSTEM WITH CLINICAL DECISION SUPPORT," all of which are hereby incorporated by reference to the extent that they are not inconsistent with the instant description.

The following description should be read with reference to the drawings, in which like elements in different drawings may be numbered in like fashion. The drawings, which are not necessarily to scale, depict selected examples and are not intended to limit the scope of the disclosure. Although examples of construction, dimensions, and materials may be illustrated for the various elements, those skilled in the art will recognize that many of the examples provided have suitable alternatives that may be utilized.

The present disclosure contemplates systems and methods of using medical devices with disposable components. While described primarily in the context of infusion pumps, the systems and methods are not so limited, and it should be apparent to those of skill in the medical device arts how the teachings of the present disclosure can be applied to medical devices other than infusion systems.

Figure 1:
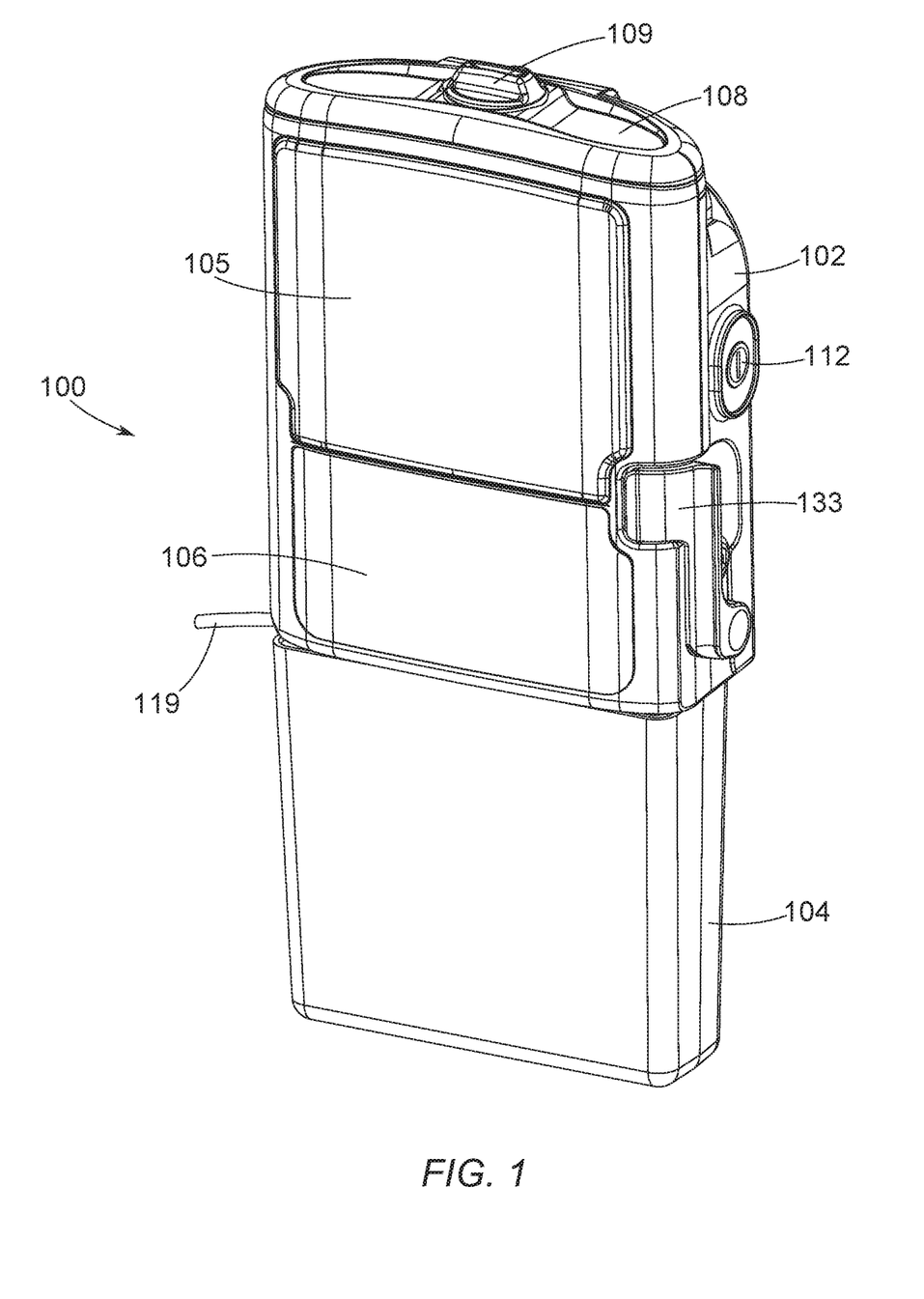
FIG. 1 is a schematic perspective view of an example embodiment of an infusion pump system that includes a control module and an optional reservoir cassette.

FIG. 1 is a schematic perspective view of an example embodiment of an infusion pump system 100 that includes a control module 102 and an optional reservoir cassette 104. Infusion pump system 100 can be a CADD® (Computerized Ambulatory Drug Delivery) Ambulatory Infusion Pump system from Smiths Medical ASD, Inc., although the teachings of the present disclosure are not limited to CADD® infusion pumps and may be practiced with other infusion pump systems, and other non-infusion medical devices.

Control module 102 of infusion pump system 100 can include a user interface having a display screen 105 and a control pad 106 (buttons, etc., of the control pad are not illustrated). Control module 102 can also include a battery door 108, including a knob 109 for locking and unlocking the door 108, which can cover a battery compartment in which batteries for powering the pump system 100 can be housed. In some examples, a combination battery and wireless communication module can be present approximately where battery door 108 is illustrated. Control module 102 can also include any or all of a power switch 112, and, visible in FIG. 2 but not FIG. 1: an input/output port 114 such as a USB port or other appropriate interface for connecting pump system 100 to a computer having software designed to interface with pump system 100, a power jack 116 for connecting a power cord for powering pump 100, and a remote dose cord jack 118 for connecting a remote dose cord that provides a way to activate patient-controlled analgesia (or "PCA") of medicament or infusate doses from pump system 100.

Example infusion pump system 100 can include a replaceable reservoir cassette 104 connected to control module 102. In an embodiment, reservoir cassette 104 can house a reservoir that in turn can contain an infusate to be delivered to a patient. Tubing 119 can extend from the cassette 104 and fluidly communicate with an infusion set or catheter (not shown) to deliver the infusate to the patient. Tubing 119 can be fluidically coupled to such an infusion set or catheter with a Luer-type connector or any other suitable connector (not shown). The control module 102 can be used to control the flow of infusate from cassette 104. One example of such a cassette is the CADD® Medication Cassette Reservoir (available in various reservoir volumes) from Smiths Medical ASD, Inc., though other cassettes and other hardware configurations can be used in other examples, as discussed further herein.

Figure 2:
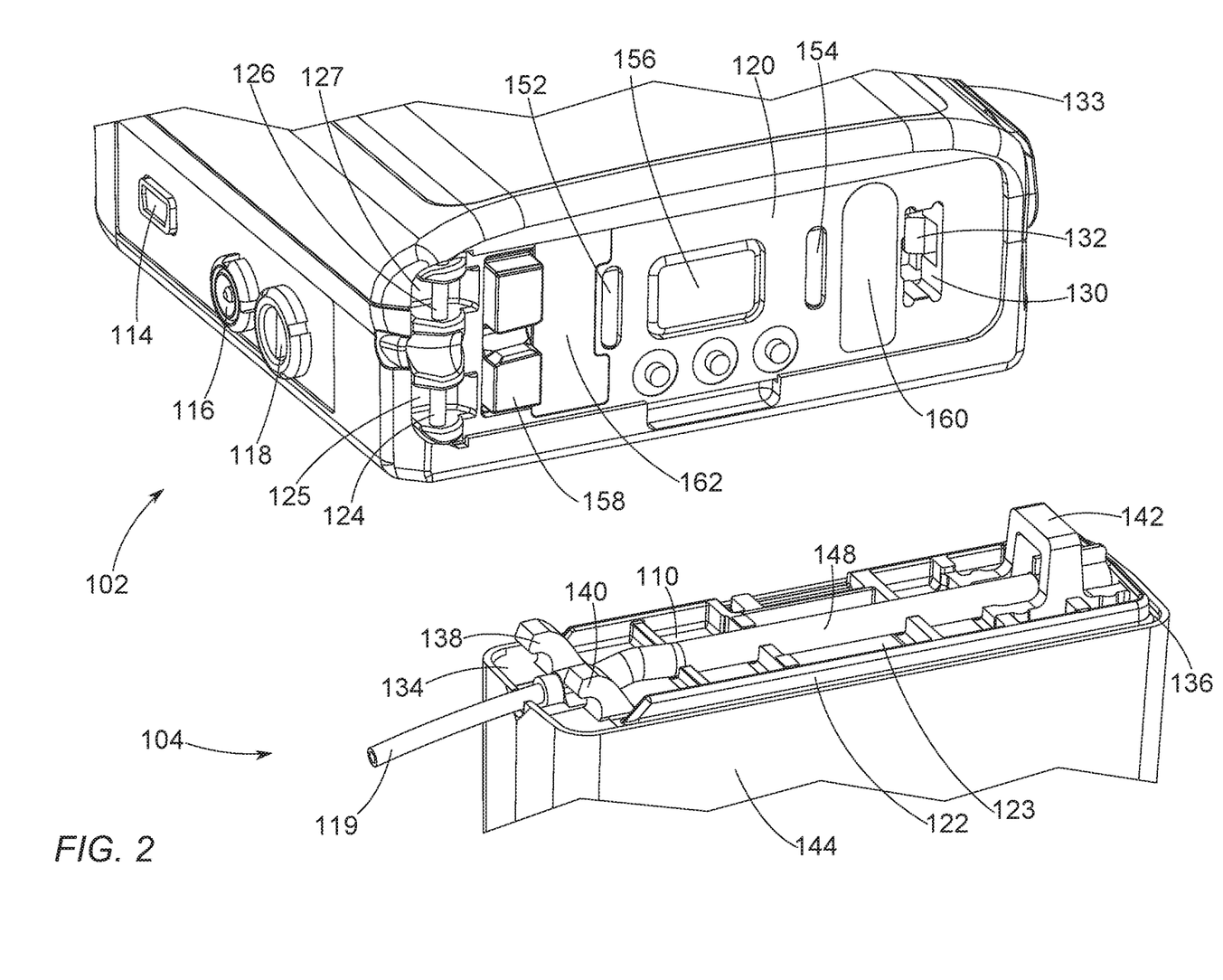
FIG. 2 is a schematic partial perspective view of the infusion pump system of FIG. 1 with the reservoir cassette separated from the control module.

FIG. 2 is a schematic partial perspective view of the example of infusion pump system 100 with reservoir cassette 104 separated from control module 102, and rotated to provide views of their mating structures. Control module 102 and reservoir cassette 104 can be configured to be reversibly connected at a mating side 120 of control module 102 and pressure plate 122 of cassette 104, respectively.

In this example embodiment, mating side 120 of control module 102 can include hinge pins 124 and 126 located proximally to a first end of mating side 120, although in other examples a single hinge pin or more than two hinge pins can be employed. Hinge pins 124 and 126 are further located in hinge wells 125 and 127, respectively.

Mating side 120 of control module 102 can include a latch receptacle 130 that is located proximally to a second end of mating side 120 opposite the first end thereof. Control module 102 can include a latch mechanism 132 associated with latch receptacle 130, and a latch lever 133 (visible in FIG. 1) to allow a user to manipulate the latch mechanism.

Pressure plate 122 of reservoir cassette 104 can include a body 123 having first 110 and second (not visible) major surfaces (top and bottom, respectively, relative to FIG. 2), a longitudinal axis and a transverse axis, first and second longitudinal sides, and first 134 and second 136 transverse ends. Pressure plate 122 can include first and second securing hooks 138, 140 extending away from first major surface 110 of body 123 proximal first transverse end 134. First and second securing hooks 138, 140 each can be structured to reversibly and hingedly couple to a corresponding one of hinge pins 124, 126. Irrespective of this example embodiment, in the present disclosure, any suitable arrangements of securing hook(s) and hinge pin(s) are contemplated.

Pressure plate 122 also can include an arch 142 extending away from first major surface 110 of body 123 proximally to second transverse end 136. Arch 142 and latch receptacle 130 of mating side 120 of control module 102 can be structured such that arch 142 is received by latch receptacle 130 as pressure plate 122 is pivoted about pins 124, 126 toward control module 102. Arch 142 can be structured to be captured by latch mechanism 132 of control module 102 and drawn toward mating side 120 of module 102 by latch mechanism 132. When arch 142 is captured by latch mechanism 132 and hooks 138, 140 are coupled to pins 124, 126, pressure plate 122 is secured thereby to control module 102.

Pressure plate 122 can be formed from any suitable material. In an embodiment, pressure plate 122 is formed from polycarbonate material, though other materials may be used. Pressure plate 122 may be joined, for example via bonding or ultrasonic welding, with a casing 144 (which may also be formed primarily of polycarbonate material) to together provide a housing of reservoir cassette 104. Reservoir cassette 104 can contain an infusate container (not shown), which may be, for example, a vinyl bag. A peristaltic tube 148 can be attached to or integrally formed with cassette 104 or the infusate container to provide a fluid path from the infusate container and cassette 104 to a patient, via, for example, downstream tubing 119 connected to peristaltic tube 148. In this example embodiment, peristaltic tube 148 can be substantially longitudinally located along first major surface 110 of body 123 of pressure plate 122, and can provide a fluid path that is substantially parallel to first major surface 110. In this example embodiment, the fluid path provided by peristaltic tube 148 can extend substantially to first transverse end 134 of body 123.

In this example embodiment, mating side 120 of control module 102 can include an air-in-line detector (AILD) 158 that partially surrounds peristaltic tube 148 (or another peristaltic tube, as discussed elsewhere herein) when reservoir cassette 104 (or other compatible component, as discussed elsewhere herein) is secured to control module 102.

AILD 158 can include a groove as illustrated within which a segment of peristaltic tube 148 resides when cassette 104 is secured to module 102. In an embodiment, AILD 158 can include at least one ultrasonic transducer located immediately adjacent to or in the groove in side 120 of module 102.

Also in this example embodiment, mating side 120 of control module 102 can include an upstream occlusion detector 160 and/or a downstream occlusion detector 162. Occlusion detectors 160, 162 can include force sensors that bear against peristaltic tube 148. Readings or data obtained from occlusion sensors 160, 162 can depend on knowledge of physical properties of the peristaltic tube 148, and possibly other properties of the infusion system upstream or downstream from the control module 102.

When reservoir cassette 104 is secured to control module 102, as illustrated in FIG. 1, module 102 can pump an infusate from cassette 104 through peristaltic tube 148 by way of a peristaltic-type pump mechanism. Tube engaging members visible in the example embodiment of FIG. 2 include downstream valve 152, upstream valve 154, and expulsor 156, which may engage and squeeze (compress) peristaltic tube 148 against pressure plate 122 in a coordinated manner to effect a peristaltic-type pumping action, as described for example in U.S. Pat. No. 4,559,038.

In another example embodiment, an infusion pump can deliver fluid from a reservoir such as an IV bag that is remote, or separate from, the control module of the pump rather than from a reservoir cassette such as cassette 104. Such a configuration can be employed, for example, when a therapy calls for a volume of infusate that is greater than the capacity of an available reservoir cassette. CADD® Medication Cassette Reservoirs are commercially available, typically, in 50 ml, 100 ml, and 250 ml volume capacities. While other capacity cassettes are possible, IV bags have an ability to provide, as compared to such cassette reservoirs, very large volumes, such as 500 ml, 1000 ml, 2000 ml, and greater.

Figure 3:
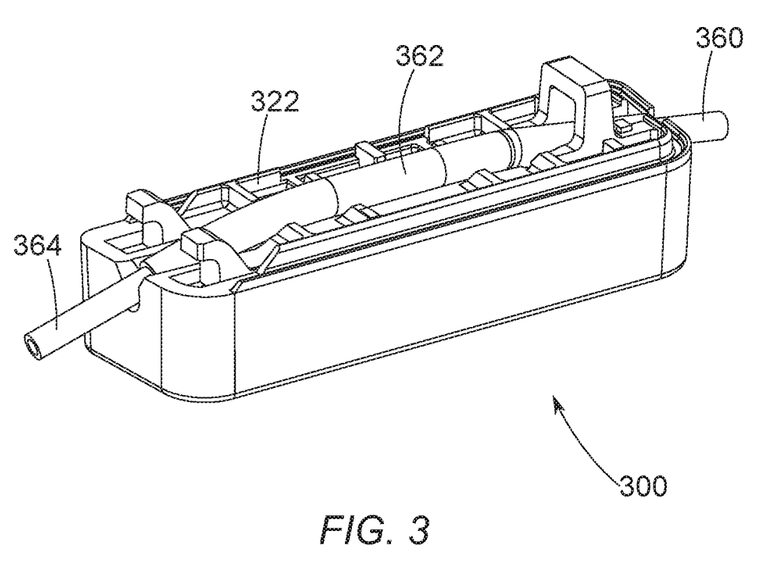
FIG. 3 is a schematic perspective view of a remote reservoir adapter.

FIG. 3 is a schematic perspective view of an example of a remote reservoir adapter ("RRA") 300 that can be employed with the aforementioned larger capacity IV bags. In this example embodiment, RRA 300 can include a pressure plate 322 that can be similar in some respects to pressure plate 122 of reservoir cassette 104. RRA 300 can include upstream tubing 360 that can extend from the IV bag (not illustrated) or other remote reservoir to pressure plate 322, where it can be fluidically coupled to a peristaltic tube 362 that extends substantially along a longitudinal axis of pressure plate 322. In this example embodiment, downstream tubing 364 can be fluidically coupled to peristaltic tube 362 opposite upstream tubing 360, and provide a fluidic path to an infusion set or catheter. Flow of infusate through such fluidically coupled segments of tubing 360, 362, 364 can be controlled by control module 102 coupled to RRA 300 in a manner similar to the coupling of control module 102 to cassette 104 as described with reference to FIGS. 1 and 2. Examples of RRAs are provided as components of CADD® Administration Sets from Smiths Medical ASD, Inc.

In some cases, different peristaltic tubes can be employed to achieve different performance objectives. For example, some therapies include relatively high rates of infusate delivery. One way to increase a delivery rate with a peristaltic pump mechanism such as that of FIG. 2 is to increase the outer diameter of the peristaltic tube. CADD® Administration Sets from Smiths Medical ASD, Inc. are commercially available, typically, in models including a standard or nominally-dimensioned peristaltic tube, as well as in "High Volume" models having a high-volume peristaltic tube. In another example, peristaltic tube geometry can be modified to improve AILD performance, as described for example in U.S. Provisional Patent Application Ser. No. 62/161,918, "SYSTEMS AND METHODS FOR IMPROVED AIR-IN-LINE DETECTION FOR INFUSION PUMPS".

The description of CADD® infusion pump systems herein provides, among other aspects, an example of a medical device system in which a main unit of a medical device (e.g., control module 102) can be used with a multitude of disposables that can have different physical properties. For example, cassette reservoirs and/or IV bags of various volumes can be used, cassettes or remote reservoir adapters with different peristaltic tubes can be employed, and different upstream and/or downstream infusion lines, linesets, catheters, etc, can be used. In other examples, other types of infusion pumps can include a main unit that can be used with various disposables that can have different physical properties. For example, a syringe-type infusion pump can be used with syringes of varying dimensions (and other properties) and a multitude of differing infusion sets. In other examples, other non-infusion medical devices are known in which a main unit can be used with a multitude of disposables that can have different physical properties, such as in the warming and monitoring systems described elsewhere herein.

Figure 4:
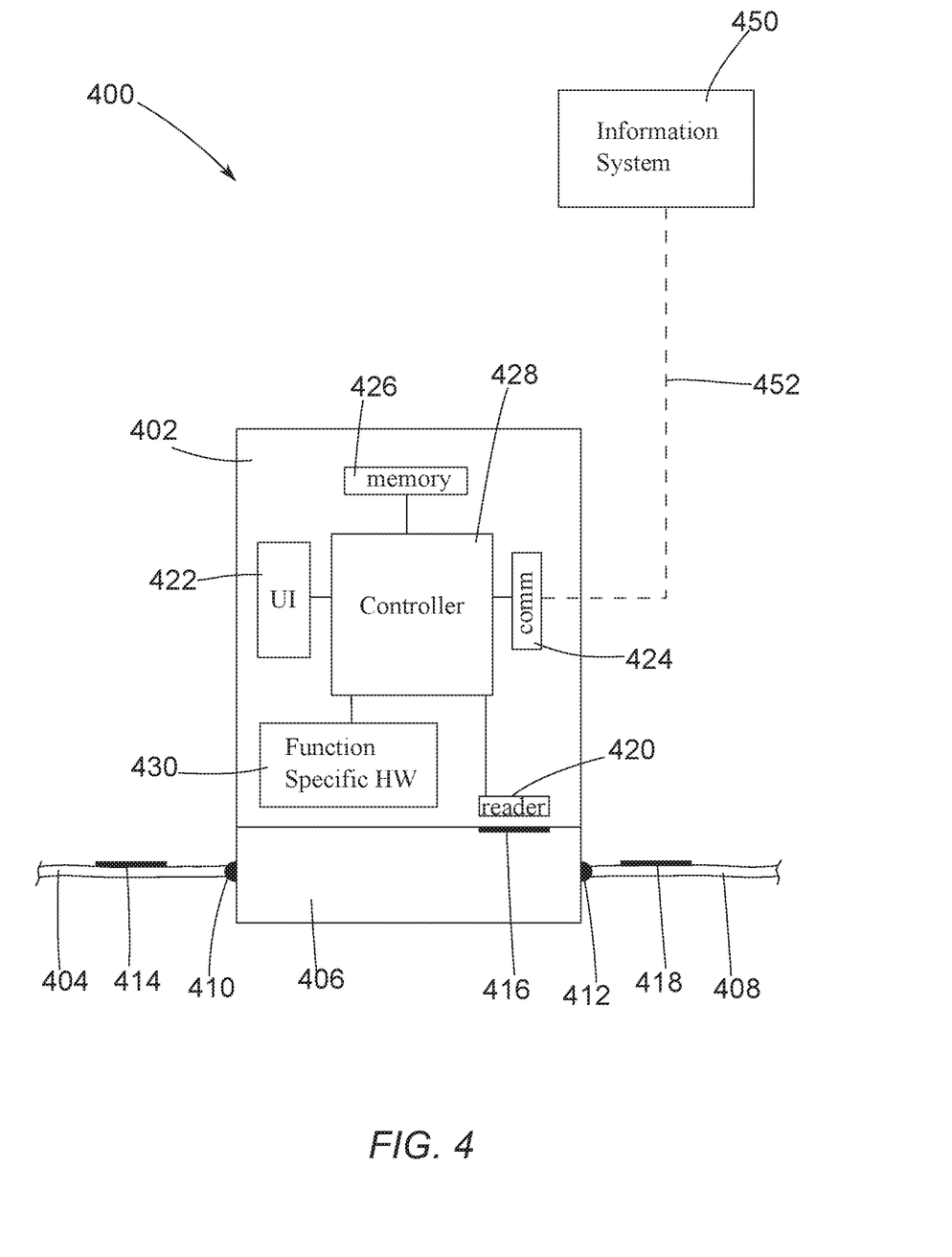
FIG. 4 is a schematic illustration of an example of a medical device system that can utilize disposables and information about disposables.

FIG. 4 is a schematic illustration of a medical device system 400 that can utilize disposables and information about disposables according to novel and inventive subject matter hereof. System 400 can include a main unit 402, which can be used in conjunction with one or more disposables 404, 406, 408. The illustration of three disposables 404, 406, 408 is merely by example and should not be considered to be limiting. In some embodiments, main unit 402 can be used with only a single disposable. In other embodiments, main unit 402 can be used with more than three disposables. While some of disposables 404, 406, 408 are illustrated as being coupled to each other, this is not necessary, and the present disclosure also contemplates main units used with multiple disposables that are not coupled to each other.

In some embodiments, main unit 402 can be a control module of an infusion pump having features similar to control module 102 of FIGS. 1 and 2, but this is not necessary. Disposable 406 can be, for example, a cassette similar to reservoir cassette 104 of FIGS. 1 and 2, or a remote reservoir adapter such as RRA 300 of FIG. 3. Disposable 404 can be, for example, an infusion set fluidically coupled to disposable 406 at a connector 410. Disposable 408 can be, for example, an upstream infusion line fluidically coupled to disposable 406 at a connector 412. These are just some examples of embodiments in which main unit 402 is an infusion pump control module similar to control module 102. In other embodiments, main unit 402 can be any other suitable type of medical device with any compatible disposable or disposables.

It is to be appreciated and understood that, as described by example or otherwise contemplated herein, medical device system 400 can include any appropriate or suitable number of main units such as main unit 402. System 400 can include a single main unit 402 or a plurality thereof. Main units could be geographically distributed in any suitable locations. System 400 could include main units within a single caregiving facility such as a hospital, or main units geographically distributed among multiple locations, where the locations could be all associated with a single healthcare organization, or could be diverse and not necessarily related locations.

Main unit 402 can include any suitable components needed or desirable to function properly as a medical device. Main unit 402 can include a built-in user interface 422 that can include hardware elements such as buttons or knobs and the like, and a display, which for example may be based upon or rely upon any suitable dynamic display technology such as a liquid crystal display (LCD), organic light emitting diode (OLED), electronic paper display (EPD), and the like, and which can be a touchscreen. In this example of FIG. 4, main unit 402 includes a communication interface 424, a memory 426, and a controller 428, which may include multiple controllers/processors. The controller 428 can be operatively coupled to any or all, or any subgrouping of, the user interface 422, the communication interface 424, and the memory 426. In some embodiments, components of main unit 402 can be integrated. The communication interface 424 can employ any appropriate communication technologies for any appropriate communication mode(s).

Main unit 402 can include any appropriate function-specific hardware 430 to provide its intended functions as a medical device. In some examples, main unit 402 can be an infusion pump, and function-specific hardware 430 can include any or all of a pump mechanism, valves, motors, drive trains, gears, couplings, sensors, application-specific integrated circuits (ASICs), firmware, and any other accessories and appropriate components. In other examples, main unit 402 can be a convective patient warmer, and function-specific hardware 430 could include a heating element, fan, motor, sensors, ASICs, firmware, and any other appropriate components.

Each disposable 404, 406, 408 can optionally include a tag 414, 416, 418, and each tag can include identifying information for its respective disposable. Disposable identifying information is discussed further elsewhere in the present disclosure. Tags 414, 416, 418 can encode or otherwise bear information about their respective disposables 404, 406, 408 in any suitable manner using any suitable technology. Main unit 402 can include a tag reader 420 that can read identifying information from one or more of tags 414, 416, 418. In some examples, tag reader 420 can read all tags included with any disposables used with system 400. In some examples, a main unit 402 can include more than one tag reader, with some tag readers suited to read tags from some disposables (for example, based on tag technology, and/or proximity of a tag reader to a tag when a disposable is attached to the main unit 402), and other tag readers more suited to read tags from other disposables. Controller 428 can be operatively coupled to tag reader(s) 420. Within a system 400, it is possible that different tag types can be used. For example, each of tags 414, 416, 418 corresponding to different types of disposables 404, 406, 408 could employ different technology and/or information encoding schemes, or one of the three could use a different scheme than the other two, etc.

Tags can employ any appropriate technology. In some examples, tags can employ radio-frequency identification (RFID) and/or near-field communication (NFC) technologies. In some examples, tags can include barcodes, QR codes, or any other optical codes, which exploit any suitable optical property or technology, such as color, holography, optical character recognition, etc. In some examples, mechanical technologies can be used to implement tags. Mechanical tag technologies can be macro- or micro-scaled, and can be static or dynamic (e.g., involving a microelectrical mechanical oscillator). In some examples, tags can exploit surface acoustic wave (SAW) technology. In some examples, tags can include integrated circuits or other electronic components that can be read via a conductive connection to a tag reader. In some examples, tags can be read without conductive connection to a tag reader. In some examples, tags can present read-only information to a reader of a main unit of a medical device. In some other examples, a main unit of a medical device can write or otherwise record information to a tag of a disposable, through a writer of the main unit, which could be integrated with the tag reader. Tags can include any suitable components for storing information, including but not limited to electronic memory components. In some embodiments, non-electronic means of writing/storing information can be employed, such as printing or otherwise mechanically marking information on a disposable.

Tag readers can employ any appropriate technology to read identifying information from tags, such as RFID technology, NFC technology, imaging and/or non-imaging optical technology, acoustic technology, mechanical sensing technology, and so on.

In some embodiments, one or more tag readers can be provided as wired or wireless external accessories (not illustrated) to a main unit, as compared with a tag reader or reader(s) provided in or on a housing of a main unit. In some embodiments, a portable device such as a smartphone or tablet computer, etc., can execute application software that uses hardware resources of the portable device to read a tag and communicate identifying information to a main unit 402 via any suitable communication mode.

Medical device system 400 can include a computing or information system or systems 450 external to main unit 402. Main unit 402 can be communicatively connected via any appropriate communication infrastructure(s) 452 to information system 450. The dashed line representing communication infrastructure(s) 452 of FIG. 4 is merely schematic and should not necessarily be interpreted as limiting the communication infrastructure(s) of the present disclosure to any particular communication infrastructure topology, technology, layers, protocols, or any other aspect(s) of how communication can be implemented. Any appropriate communication devices such as, for example, routers or repeaters can be employed in communication infrastructure(s) 452. In systems 400 that include multiple main units, communicative connections between different main units and the information system can be made by different means. For example, one main unit could be communicatively connected through communication interface 424 to information system 450 via a wired connection (such as Ethernet or any other suitable protocol) exclusively or in combination with one or more other modes of connection, and another main unit could be communicatively connected to information system 450 via an unwired connection (such as WiFi or any other suitable protocol) exclusively or in combination with one or more other modes of connection. These are just some examples. The systems and methods of the present disclosure can include and be implemented by and with any communication infrastructure 452 suitable to realize the functions of the systems and methods, and should not be considered limited to any particular communication architecture unless specifically described as such.

It is to be appreciated and understood that computing or information system 450 could reside or be hosted in any appropriate location. Information system 450 should not necessarily be considered to be limited to a single physical device (although in some embodiments it may be), but rather, any suitable system or arrangement of one or several components can be used to provide an information processing capability, such as one or more processes being executed by a networked system of servers. In some embodiments, medical device system 400 can include more than one information system. As such, in some embodiments of the present disclosure "information system 450" may refer to multiple information systems. In some embodiments, information system 450 can be provided or hosted by a manufacturer, such as a manufacturer of main unit 402 and/or one or more of disposables 404, 406, 408. In some embodiments, information system 450 can be provided or hosted by a caregiving facility such as a hospital, or a healthcare organization, or a regulatory or governmental authority. These are just some examples. Information system 450 can be provided or hosted by any suitable organization or entity.

As a matter of semantics, it is to be appreciated and understood by those of ordinary skill in the art that in the present disclosure, a relatively colloquial statement such as "a main unit 402 reads a tag 414, 416, 418 and transmits information read from the tag to an external information system 450" should be interpreted in the context of the systems and methods as described herein, and should not be considered unduly limiting because of the colloquial nature of its expression. For example, to read a tag 414, 416, 418, a controller 428 of main unit 402 may execute software instructions present in memory 426 that instruct the reader 420 to read the tag and transfer information read from the tag into memory. Transmitting information read from the tag 414, 416, 418 can include the controller 428 executing software instructions to retrieve the information read from the tag from memory and transmit it via communication interface 424 to information system 450. Other translations from colloquial expressions to more technically precise descriptions should be readily apparent to those of ordinary skill in the art.

In the present disclosure, the various described capabilities of associating identifying information with disposables, such as by the examples of tags, reading or otherwise ascertaining information from the tags by a medical device main unit, and transferring information between the medical device main unit and an external information system, can be used in systems and methods of the present disclosure to result in advantageous operation of medical device systems overall.

Systems and methods of the present disclosure can involve a variety of kinds of information about disposables. Any particular individual disposable can have multiple items of information associated with it. The information can advantageously have various applicability to disposables. For example, some information can apply to all disposables of the same model (e.g., disposables from a manufacturer that share the same stock keeping unit [SKU]) while other information can apply to subgroups of disposables of the same model (e.g., disposables sharing a SKU that were manufactured in a particular lot), and yet other information can apply to a particular individual disposable (e.g., a manufacturer-assigned serial number). Some information can apply to other groupings of disposables, such as groupings of disposables of different models (e.g., all disposables purchased by a particular hospital on a given purchase order, or disposables from a single manufacturer in a given product category, or any other grouping). These are just some examples, and other groupings of applicability of information about disposables can be advantageously employed in particular situations.

Any information that pertains to a disposable can be considered identifying information for the disposable. Depending on the degree of applicability of a particular item of identifying information, it can serve to resolve the identity of the disposable to the degree of the applicability of the information. For example, model information can identify a disposable as being a certain model of disposable, lot information can identify the manufacturing lot of a disposable, unique identifying information can identify an exact single disposable, and so on. Depending on how identifying information is to be used, as discussed further herein, systems and methods of the present disclosure can obtain, read, or ascertain identifying information to an appropriate or desired level of resolution. For example, for some purposes, only model information would be used, while for other purposes, information identifying a unique individual disposable would be used.

Identifying information for a disposable can include any of a name, code, SKU, identifier, etc., that identifies the precise model of the disposable. Identifying information can include properties of the model of disposable. For example, if the disposable is a model of reservoir cassette for an infusion pump, such as a CADD® Medication Cassette Reservoir, identifying information could include the volume of the reservoir, the volume of infusate delivered per motor cycle, the priming volume for the reservoir, downstream occlusion detection parameters, air detection parameters, compatibility with types of infusates, compatible route(s) of infusion, chemical and/or physical properties of the reservoir, or any other characteristics of the reservoir. If the disposable is a model of administration set, such as a CADD® Administration Set, identifying information could include any applicable information as listed above for reservoir cassettes and could further include upstream occlusion detection parameters and any other characteristics. Other information could include whether the disposable includes any special characteristics for particular applications, such as whether it is a low absorption or a light blocking disposable. Identifying information could include information about chemical compatibility. In other examples, the disposable could be a warming blanket for use with a convective heater/blower. Identifying information relating to blanket models could include the type of blanket (e.g., underbody, gown, infant, etc.), flow rate parameters, and any other characteristics. These are just some examples of identifying information for certain kinds of disposables. Analogous types of information for other kinds of disposables, applicable at the model level, will be apparent for those of skill in the relevant art areas.

Identifying information for a disposable can include information about specific subgroups of disposables of the same model. Such information could include, as mentioned elsewhere, identification of a specific manufacturing lot. It could also include information about the manufacturer, date/time of manufacture, location of manufacture, batches of material used in production, and any other characteristics. In some cases, it could include calibration or other performance parameters for the disposable that could vary from production lot to production lot. In some cases, identifying information could include shipment information, and/or could include information about the environmental conditions to which the group of disposable has been subjected. Such environmental condition information could be indirectly inferred from, for example, shipping history, and/or it could be derived directly from sensors accompanying a shipment, such as temperature, humidity, acceleration, etc. sensors. Data from such sensors could be reported to an information system and associated with groups of disposables.

Identifying information for a disposable can include information that applies to the disposable at the individual unit level. One type of such information is identifying information that uniquely identifies each disposable individually, such as a serial number. Such information, which in the present disclosure may be referred to as "unique identifying information," could be assigned to disposables by any appropriate organization, authority, or other body, such as manufacturers, standards bodies, regulatory agencies, etc. Unique identifying information can incorporate cryptographic and/or authentication measures to (attempt to) ensure that an individual disposable can be reliably associated with its unique identifying information.

Identifying information that applies to the disposable at the individual unit level can include types of information other than unique identifying information, such as calibration or other performance parameters for the individual disposable, or information about the history of the individual disposable such as geographic movements of the disposable, use history of the disposable, environmental conditions the disposable has experienced (which could be measured by sensors of the disposable), and so on. Identifying information about an individual disposable can include information relating to a specific actual use of the disposable, such as patient identification and/or other patient information (age, gender, height, weight, condition, allergies, disease, etc.), caregiving facility information, infusate(s) being used, infusion route, infusion delivery protocol and or parameters, other therapy information, etc. In the case of an infusion reservoir, identifying information relating to a specific actual use of the reservoir can include when, where, how and/or by whom the reservoir was filled, with what infusate the reservoir was filled, the volume of infusate with which the reservoir was filled, etc.; and if the reservoir is or has been in use: how much infusate has been delivered, and how much infusate remains (which could be useful if the reservoir is switched between pumps). These are just some examples, and any suitable information can be associated with an individual disposable.

In systems and methods of the present disclosure, identifying information for disposables can be stored and handled in any appropriate manner. As described in further detail herein, in reference to example medical device system 400 of FIG. 4, identifying information can be stored in or on tags 414, 416, 418 of disposables 404, 406, 408, in memory 426 of main unit 402, and/or in or on information system 450 (which can represent more than one information system). Identifying information about a disposable can be stored and/or handled by multiple devices of medical device system 400. As further discussed herein, identifying information about a disposable at one device can point to further identifying information about the disposable at another device.

In many embodiments, tags 414, 416, 418 of disposables 404, 406, 408 can include unique identifying information that can be read from the tags by a reader 420. In some embodiments, unique identifying information can be the only information on the tags. In some embodiments, any or all of the kinds of identifying information relating to disposables described herein can be included on a tag of a disposable. In some cases, however, limitations of tag technology and/or format can constrain the amount of information that can be stored on a tag, and it may be impractical or impossible to store all desired identifying information relating to a disposable on the tag of the disposable. In some embodiments and as aforementioned, unique identifying information read from a tag of a disposable can be used as a pointer to identifying information about the disposable that is stored on a device or in a location other than the tag, such as in memory 426 of main unit 402, and/or in or on information system 450.

Any suitable distribution of information among devices (tags 414, 416, 418; main unit 402; information system 450) and transfer of information between devices can be practiced in systems and methods of the present disclosure. In some embodiments, a main unit 402 reads only unique identifying information from a tag 414, 416, 418 of an attached disposable 404, 406, 408. The unique identifying information can used by the main unit 402 to access identifying information about the disposable 404, 406, 408 from any device of the system where such information is located.

In some embodiments, a main unit 402 can read unique identifying information from a tag 414, 416, 418 of a disposable 404, 406, 408 and can transmit information relating to the unique identifying information to information system 450, which can respond by transmitting identifying information about the disposable back to the main unit, which can store the information in its memory 426 for further use. Such a process can include any suitable intermediate steps. For example, transmitting information relating to the unique identifying information to information system 450 can include transmitting said information to a "directory" or "lookup" server that, presented with information relating to the unique identifying information, provides identifying information about the disposable (such as model information) that can be used to access further identifying information from another server of the information system. In another example, information system 450, when presented with unique identifying information about a disposable 404, 406, 408 from a main unit 402, can provide information pertaining to the individual disposable such as calibration or other performance parameters.

In some embodiments, a main unit 402 can store in its memory 426 a library or collection of information about a plurality of disposables, for example, information about disposables organized by model. In some of these embodiments, the main unit 402 can read identifying information from a tag 414, 416, 418 of a disposable 404, 406, 408 and subsequently access information about the disposable from the library stored in its memory 426 based upon the read identifying information. In some others of these embodiments, further step might be needed before information about the disposable can be retrieved from the library stored in memory 426. In such an embodiment, a main unit 402 could read unique identifying information from a tag 414, 416, 418 of a disposable 404, 406, 408 and then transmit information relating to the unique identifying information to information system 450, which could respond by transmitting information identifying the model of the disposable back back to the main unit, which could then use the information about the model to access information about the particular model of disposable from the library of information about disposables stored in memory 426.

In some embodiments, a main unit 402 reads information identifying the model from a tag 414, 416, 418 of a disposable 404, 406, 408 and subsequently uses the information about the model to access information about the particular model of disposable from either or both of a library of information about disposables stored in memory 426 of the main unit, and/or from information system 450.

In some embodiments, a main unit 402 reads unique identifying information from a tag 414, 416, 418 of a disposable 404, 406, 408, as well as calibration or other performance parameters pertaining to the individual disposable. Use of the calibration or other performance parameters, which could be in a condensed form due to memory constraints, could require additional model-specific information that the main unit 402 can access from its memory 426 and/or information system 450.

These are just some examples of how identifying information for disposables can be distributed among, and accessed from, devices of a medical device system.

In some embodiments of the present disclosure, systems and methods of handing identifying information for disposables can be used that do not necessarily include the afore-described tags on disposables. In some embodiments, a main unit 402 of a medical device system 400 can obtain identifying information about one or more disposables 404, 406, 408 by receiving user input via a user interface 422 of the main unit. Any suitable user interface implementation(s) can be used for input of identifying information by the user(s). Some user interface implementations can include a user entering alphanumeric information, which can be any appropriate information, into the user interface. The alphanumeric information could, for example, be read from the disposable 404, 406, 408 by the user, and could be a model number or unique identifying information. Some user interface implementations, perhaps more user friendly, can include the user entering identifying information via a menu presented on a display of the user interface 422. The menu could be presented in any suitable format, and could be a hierarchical menu that prompts the user to enter progressively more specific information. For example, the menu system could start by asking the user to identify the type of disposable 404, 406, 408 (for a medical device system 400 usable with more than one type), then progress to other characteristics, such as capacity, high vs. low flow, and any other salient characteristics. In some examples, a graphical user interface can allow a user to select disposable components in a pictorial manner that represents the actual physical appearance of the disposables, and possibly the main unit; in some such graphical user interfaces, a user could "assemble" the system of main unit and disposable as it physically appears in real life. In some examples, a user interface 422 could include spoken word input for disposable identifying information. In some embodiments, a camera of a main unit 402 could image disposables and the models of disposables could be identified via image recognition. These are just some examples, and other user interface schemes for inputting identifying information for disposables are possible.

As described herein, systems and methods of the present disclosure include the use of identifying information for disposables in medical device systems, providing a variety of advantages over prior systems and methods that do not so use disposable identifying information. In exemplary medical device system 400, identifying information for disposables 404, 406, 408 can be used by main unit 402 of medical device system 400 in any suitable manner for any appropriate purpose.

In some embodiments, identifying information for disposables can be used to assess whether disposables are valid for use, and in some cases, allow or not allow use of disposables based upon determinations of validity. Determinations of whether disposables are valid for use can be based upon any suitable criteria. In some embodiments, one or more entities can maintain one or more lists of disposables that can include information relating to the validity for use of the disposables. Any appropriate entities can be involved in the maintenance of the list(s) of disposables, such as manufacturers, regulatory and/or governmental authorities, healthcare organizations, and so on. In some embodiments, more than one list can be maintained: for example, one by a medical device manufacturer, another by a healthcare organization. Lists with disposable validity information can be maintained in any suitable location, such as information system 450. It is contemplated that a medical device could compare identifying information read from a disposable with validity information on such a list to determine whether a disposable is valid for use. Such systems and methods can provide the benefit of permitting only the use of disposables that are manufactured by an appropriate manufacturer, are not expired or excessively aged, and are not subject to recalls or conditions, etc., that may contraindicate use.

Figure 5:
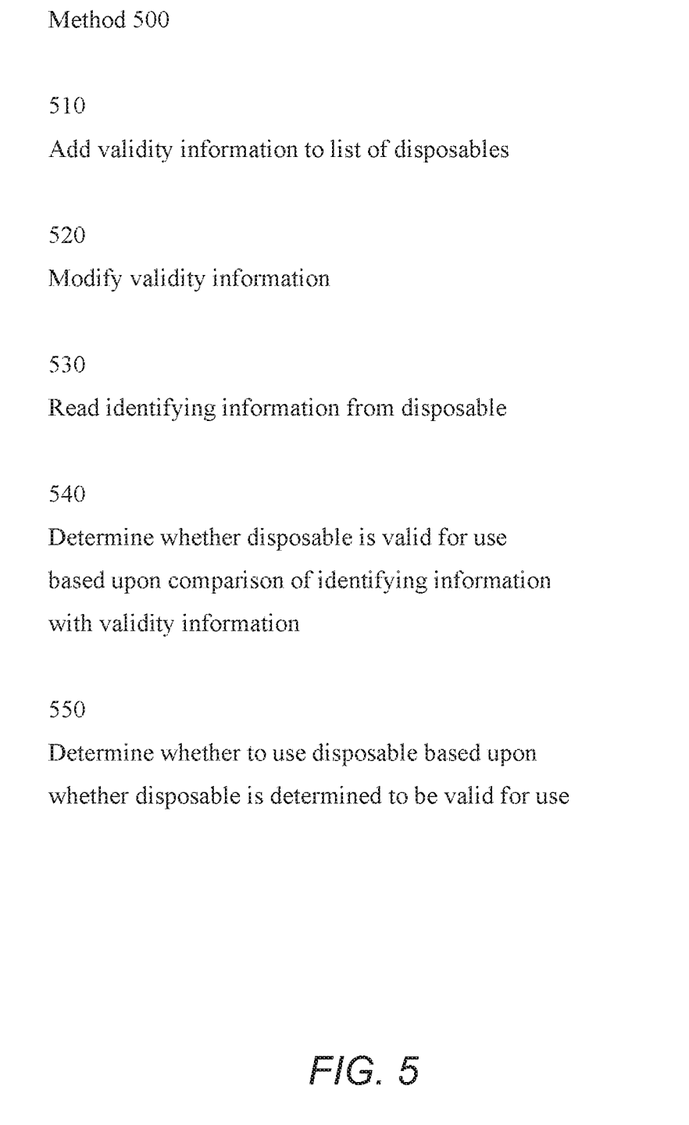
FIG. 5 is a flow diagram of an illustrative example of a method for managing use of a disposable with a medical device that includes the use of a list with validity information.

FIG. 5 is a flow diagram of an illustrative example of a method 500 for managing use of a disposable with a medical device that includes the use of a list with validity information. At 510, the method can include adding validity information about one or more disposables to a list of disposables. In some examples, a manufacturer can add validity information that identifies disposables individually, using unique identifying information. Alternately, or in addition, a manufacturer could identify disposables in the aggregate, for example, by manufacturing lot. Validity information can be any suitable information that can be used to establish the validity for use of a disposable (or set of disposables). Method 500 can include at 520, subsequent to adding the validity information to the list, modifying (by, for example, an entity such as a manufacturer or regulatory agency) validity information on the list of disposables. Such modification could be performed for any appropriate reason. In some instances, validity information for disposables subject to a recall could be modified. In another scenario, validity information pertaining to an expiration date for disposables could be modified if accelerated aging testing indicated that the disposables would remain safe for use longer than previously had been established. In another example, discovery of counterfeit disposables could lead to adding validity information to the list of disposables with identifying information to block use of the counterfeits.

At 530, method 500 can include a main unit reading identifying information from a disposable. Reading the disposable can be performed at any suitable time. For example, it could be performed by the main unit automatically as or after the disposable is connected to the main unit, as part of a power-up or initialization routine, and/or upon entry of a command from a user, or at any other appropriate time. At 540, method 500 can include determining whether the disposable is valid for use. This determination can be based at least in part upon comparison of the identifying information read from the disposable by the main unit with the validity information on the list of disposables. The determination could be performed by the main unit, and/or it could be performed by an external information system.

In some embodiments in which the determination of whether the disposable is valid for use is performed by a main unit, the main unit can retrieve validity information about the disposable from an external information system on which the validity information is stored, with such retrieval of information taking place substantially during the determination. In some other embodiments in which the determination of whether the disposable is valid for use is performed by a main unit, the main unit can download validity information from an external information system and store such information in the main unit's memory before the determination is performed. Such an arrangement can make it possible for a main unit to use validity information subsequently for a determination even if it cannot communicate with the external information system during the determination. Such downloads of validity information could be performed with any appropriate timing. For example, downloads could be performed on a regular schedule, and/or on the command of a user and/or potentially every time a communication link between the main unit and external information system is established. Downloads could be initiated with a request from the main unit to the external information system, and/or they could be initiated by the external information system ("pushed" from the external information system to the main unit). Other suitable downloading arrangements for validity information are possible.

The determination of validity at 540 can include consideration of any appropriate information, including identifying information and validity information on any relevant list of disposables. Without limitation, the determination of validity at 540 can include determining whether or not the disposable is from an appropriate manufacturer, is under recall, is expired, and/or has been used previously (discussed in further detail elsewhere herein). The determination of validity at 540 can also include consideration of disposable identifying information in relation to the application for which the disposable is to be used, such as (in the case of infusion systems) whether the disposable is intended for the specified route of infusion, and/or whether the disposable has appropriate properties for the infusion, such as being a low absorption and/or a light blocking disposable, or any other relevant properties. Also in the case of infusion systems, if a drug library is in use, the determination of validity at 540 can also include verification that the disposable is identified for use by the current drug library selection. In some cases, geolocation and/or other position determination technology could be used to restrict the use of certain disposables to certain locations, such as at particular healthcare facilities, or even particular locations within a healthcare facility.

Based at least in part upon the determination of whether the disposable is valid for use, at 550 the method can include the main unit making a determination of whether or not to proceed with use of the disposable. In the case of an infusion pump, for example, the determination could be whether to deliver or not deliver an infusate with infusion disposables such as an infusion administration set and/or reservoir cassette. In the case of a convective warmer, the determination could be whether to provide or not provide warm air to a disposable blanket. In some embodiments, the determination of whether or not to proceed with use of the disposable could be made by information system 450.

In some cases, determining whether or not to proceed with use of a disposable (at 550) can depend on more information than solely the determination (at 540) of whether the disposable is valid for use. In some embodiments, a main unit can notify a user that a disposable has been determined to be not valid for use. This can include notifying the user of a specific reason that the disposable has been determined to be not valid for use (such as that the disposable is subject to a recall, or is not from a valid manufacturer, or has been used before, etc.). The main unit can allow the user to specify use of the disposable despite the determination that the disposable is not valid for use, and then the main unit can proceed with use of the disposable. In some embodiments, this specification by the user could be required in every case that a disposable is determined not to be valid for use, or in other embodiments the user could be allowed to enter a blanket over-ride to always use disposables regardless of whether or not they have been determined to be valid for use. In some embodiments, a medical device system that allows a user to specify use of a disposable or disposables that has/have been determined not to be valid for use can log, record, and/or report, etc., information about the override or approval-for-use of the disposable, such as the identity of the user, and/or a reason or explanation for the override/approval. In some embodiments, a determination of whether to use disposables that have been determined to be not valid for use could be made by or at an entity other than the main unit, for example, at the healthcare institutional level, via information system 450.

Method 500 of FIG. 5 can be extended to include the use of multiple disposables with identifying information. Determining at 540 whether a disposable is valid for use can be extended to determine whether a combination of multiple disposables are valid for use together, which can include determining whether the multiple disposables are mutually compatible.

In some embodiments, method 500 can include a main unit reporting (for example, to an external information system) an association between the main unit, the disposable(s) in use, the infusate (if an infusion system), a facility code, a location code, a patient identifier, and/or any other appropriate information.

In some embodiments a main unit 402 could be configured and programed to display, automatically and/or by request, any disposable identifying information that could be relevant to patient safety, including "five rights" information, and information about infusates contained by a disposable that is a reservoir, including (but not limited to) such types of information listed elsewhere herein, such as when, where, and/or by whom the reservoir was filled, with what the reservoir is filled, and so on. Displaying such information for review by medical personnel could provide a valuable safety check. Such information could be displayed automatically, for example, when a disposable 404, 406, 408 is coupled to a main unit 402, and/or before a therapy is initiated.

In some embodiments, identifying information for disposables can be used to restrict a disposable to a single use. In some embodiments, information stored on a "writable" tag such as a writable RFID or NFC tag can be used to indicate whether a disposable has been used, with a main unit being configured to write to the tag when the disposable is used. Upon subsequent attempted use, a main unit could read the tag indicating the prior use of the disposable, and further use could be prevented. Any suitable scheme of encryption, etc., could be employed to prevent intentional circumvention of such a system.

Systems and methods to prevent disposable re-use do not necessarily require writable tags. In some embodiments, information about the use of unique individual disposables can be recorded by an information system external to a main unit and attached disposables. For example, in reference to method 500 of FIG. 5, validity information can include information about prior disposable use, and determining (at 540) whether the disposable is valid for use can include determining whether a disposable has been used previously according to the validity information. When a disposable is used by a main unit, the main unit can communicate with the external information system to indicate the use of the disposable. Information provided in such a communication can be included in modifying validity information (at 520, for example). Any suitable scheme of encryption, etc., could be employed to prevent intentional circumvention of such an information system-enabled system of multiple-use prevention.

In some embodiments, it is envisioned that after (or even possibly during) use of a disposable, a main unit could communicate information to an external information system regarding the performance of the disposable, particularly if the performance of the disposable deviated from expected norms. For example, a disposable could include a moving part or parts actuated by a motor of the main unit. If the main unit encountered greater friction in the disposable, which for example could indicate a manufacturing issue, or a degradation of lubricant potentially stemming from environmental conditions during shipping or handling, the main unit could communicate this to the external information system. As a possible consequence, validity information could be modified, such as indicating that a manufacturing lot or a shipping lot is suspect and may be compromised. In some embodiments, a main unit could modify locally-stored validity information (such as in the main unit's onboard memory), in response to observing performance of a disposable deviating from expected norms, without necessarily communicating with an external information system. Based upon its locally-stored validity information, the main unit could then modify or stop its use of disposables from a group of disposables (e.g., a box or a lot, etc.) from which the deviant-performing disposable originated.

In some embodiments, main unit 402 can modify one or more operating parameters based at least in part upon identifying information read from a tag 414, 416, 418 of a disposable 404, 406, 408 by the main unit. The identifying information can be information that applies to the disposable 404, 406, 408 at any relevant level. For example, the main unit 402 can modify one or more operating parameters based upon identifying information that applies at the level of the model of the disposable 404, 406, 408. In an example of an infusion system where the disposable is a reservoir cassette for an infusion pump, model-level information could include parameters relating to the volume of infusate delivery per motor cycle, and/or parameters relating to occlusion detection (such as back pressure) and/or air-in-line detection. In an example of a convective heating system, model-level information could include the type of blanket, such as over-body, under-body, gown, etc., which could then establish appropriate flow rates, temperatures, etc., for the blower.

In some examples, the main unit 402 can modify one or more operating parameters based upon identifying information that applies at the individual unit level of the disposable 404, 406, 408, such as calibration parameters that vary from unit-to-unit. Modifying operating parameters based upon calibration parameters for individual disposables can help reduce production costs by compensating for wider variety in disposable production (i.e., disposables can be produced with wider tolerances if the variation can be compensated for with calibration). In examples where the disposable includes a battery or other energy storage device, the main unit could modify operating parameters based upon the battery state. In some cases, operating parameters can be modified based upon information about an individual use of the disposable, such as details of a therapy for an individual patient.

In relation to method 500 of FIG. 5, the modification of operating parameter(s) can take place at any time that the main unit is in possession of identifying information needed to enact the modification of operating parameters, which could be the case before and/or after the determining actions. In some other embodiments, a main unit can modify operating parameter(s) in a method or process that does not necessarily include the determining action(s) of method 500.

It is to be understood that while the modification of one or more operating parameters can be based upon identifying information read from a tag 414, 416, 418, not all information used as input to the modification of operating parameters need necessarily be read from the tag. As described herein, identifying information read from a tag 414, 416, 418 can be used as a pointer to identifying information elsewhere in medical device system 400, such as in memory 426 of main unit 402, and/or in information system 450. In some embodiments, a main unit can modify one or more operating parameters based at least in part upon identifying information that is not read from a tag. Such identifying information could be entered, for example, via user interface 422 of main unit 402, as described elsewhere herein.

Modification of operating parameter(s) of a main unit 402 based upon identifying information associated with a disposable 404, 406, 408 can include selecting application software for the main unit to execute in conjunction with the disposable. For example, a main unit 402 that is an infusion pump could select from application software for epidural procedures, enteral procedures, intravenous (IV) procedures, or other specific infusion procedures, based upon identifying information denoting that the disposable(s) 404, 406, 408 being used with the main unit is/are configured for a corresponding procedure. The application software could include the use of visual cues (such as, but not limited to, color) on the main unit 402 to indicate the specific application corresponding to the disposable(s) 404, 406, 408 being used. For example, in some healthcare environments, a yellow color scheme is commonly identified by medical practitioners as pertaining to epidural procedures, and an orange color scheme is commonly identified by medical practitioners as pertaining to enteral procedures. (It should be noted that these color associations are not universal and may vary between hospitals, institutions, regions, practices, etc.) Disposables 404, 406, 408 could be colored yellow, or orange, etc., and the corresponding selected application software could display the same color on a user-interface 422 screen of the main unit 402, providing medical personnel with quick visual safety check that could make a match or mismatch between main unit programming and disposables readily apparent. International Patent Application No. PCT/US2015/038309, titled "MEDICAMENT INFUSION SYSTEM AND PUMP ASSEMBLY FOR USE THEREIN", having an assignee in common with the present disclosure, describes, among other things, aspects of infusion systems in which a medical device configuration can be selected to correspond to attached physical hardware. Disposable identifying information handling systems and methods as described in the present disclosure can be applied to the systems and methods of International Patent Application No. PCT/US2015/038309 in order to, among other functions, identify to the infusion pump the mode of infusion therapy corresponding to the attached physical hardware.

U.S. Provisional Patent Application Ser. No. 62/139,289, titled "MEDICAL DEVICE CONTROL", having an assignee in common with the present disclosure, describes, among other things, a disposable or replaceable component of a medical device having an application-specific control panel that includes a wireless responder that can be interrogated by a medical device. Disposable identifying information handling systems and methods as described in the present disclosure can be applied to the systems and methods of U.S. Provisional Patent Application Ser. No. 62/139, 289 in order to make identifying information corresponding to the disposable or replaceable component available to the medical device.

Figure 6:
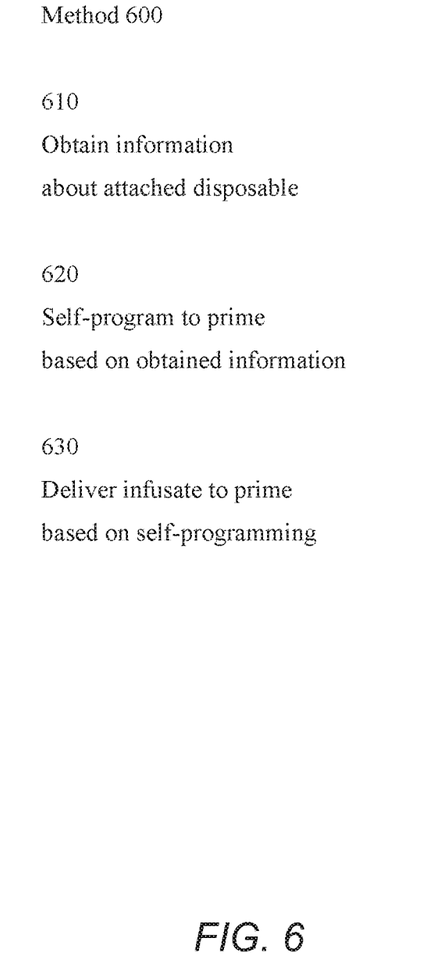
FIG. 6 is a flow diagram of an illustrative example of a method for managing use of a disposable with an infusion pump.

In some embodiments, an infusion pump can program itself to prime disposables based upon identifying information of one or more disposables being used. Any relevant identifying information can be used as input information for the programming, such as tubing size(s), the volume of infusate needed to flush an infusion line (flushing volume or priming volume or "dead space"), and the volume of infusate pumped per cycle of a peristaltic pump mechanism. In some examples, multiple disposables can be used (for example, disposables 404, 406, and 408 of FIG. 4 all can be infusion disposables needing to be primed before a therapy is commenced), and the volume of infusate needed to prime the infusion system can be an aggregate volume for the multiple disposables. FIG. 6 is a flow diagram of an illustrative example of a method 600 for managing use of a disposable with an infusion pump. At 610, method 600 can include an infusion pump obtaining identifying information about an attached disposable or disposables. At 620, method 600 can include the infusion pump self-programming to deliver infusate sufficient to prime the disposable(s), with the self-programming being based at least in part upon the identifying information. Based upon the self-programming, at 630 method 600 can also include the infusion pump delivering infusate sufficient to prime the disposable(s). In some embodiments, the infusion pump obtaining identifying information can include a reader of the infusion pump reading a tag(s) of the disposable(s). In some embodiments, the infusion pump obtaining identifying information can include receiving user input via a user interface of the infusion pump. In some embodiments, a combination of tag reading and user input can be employed. Method 600 can include, at any appropriate place(s), user input to initiate and/or approve actions. For example, in some embodiments, a user can be required to request that the infusion pump self-program to prime disposables before self-programming is performed, and/or a user can be required to confirm the appropriateness of self-programming before initiating an infusate delivery priming sequence based upon the self-programming. Self-programming for disposable priming can significantly simplify workflows for caregivers, who without self-programming may be required to assess priming requirements of an infusion system and manually enter a program, or sometimes, multiple programs, to prime the infusion system with each use of the system.

In some embodiments, identifying information of one or more disposables being used in treatment of one or more patients concurrently can be advantageously employed to efficiently coordinate practitioners' workloads and work flows. For example, International Patent Application No. PCT/US2014/044586, titled "INFUSION PLANNING SYSTEM" and U.S. Provisional Patent Application No. 62/095,522, titled "INFUSION PLANNING SYSTEM WITH CLINICAL DECISION SUPPORT", each having an assignee in common with the present disclosure, describe, among other things, devices, systems and methods for coordination of medical care and planning, visualization, staffing, delivery, resource allocation, and documentation tools for medical care, including management of patient infusion pumps, in hospitals and other medical care facilities. These patent applications also describe, among other things, devices, systems, and methods for "on the fly" or "real-time" adaptability in scheduling and efficiency in making adjustments resulting from deviations from scheduled patient treatments. In particular, in some embodiments of the novel and inventive subject matter of the present disclosure, identifying information of one or more disposables being used for a planned therapy of a patient, or for planned therapies for several patients concurrently, could be input to the planning systems of the aforementioned patent applications. The planning systems could then advantageously transmit such identifying information to a pharmacy for more efficient demand planning and physician order forecasting, for example, as deviations or changes in previously planned patient therapies occur.

Persons of ordinary skill in arts relevant to this disclosure and subject matter hereof will recognize that embodiments may comprise fewer features than illustrated in any individual embodiment described by example or otherwise contemplated herein. Embodiments described herein are not meant to be an exhaustive presentation of ways in which various features may be combined and/or arranged. Accordingly, the embodiments are not mutually exclusive combinations of features; rather, embodiments can comprise a combination of different individual features selected from different individual embodiments, as understood by persons of ordinary skill in the relevant arts. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

The invention claimed is:

1. A method for managing use of a disposable with an infusion pump, comprising:
    adding validity information about a particular set of disposables to a list of disposables;
    modifying the validity information about the particular set of disposables on the list of disposables, subsequent to adding the validity information;
    an infusion pump reading identifying information from a disposable;
    determining whether the disposable is valid for use, based at least in part upon comparison of the identifying information read from the disposable by the infusion pump with the validity information about the particular set of disposables on the list of disposables;
    the infusion pump making a determination of whether to deliver or not deliver an infusate based at least in part upon the determining whether the disposable is valid for use;
    allowing a user to override a determination to not deliver an infusate and to specify use of the disposable despite the determination that the disposable is not valid for use; and
    the infusion pump delivering the infusate if the user specifies use of the disposable, without changing the validity information.

2. The method of claim 1, further comprising the infusion pump notifying a user that the disposable has been determined to be not valid for use.

3. The method of claim 2, wherein notifying the user that the disposable has been determined to be not valid for use includes notifying the user of a specific reason that the disposable has been determined to be not valid for use.

4. The method of claim 1, further comprising the infusion pump modifying at least one operating parameter based at least in part the identifying information read from the disposable by the infusion pump.

5. The method of claim 4, wherein the at least one operating parameter relates to occlusion detection.

6. The method of claim 1, further comprising:
    the infusion pump self-programming to deliver infusate sufficient to prime the disposable, the self-programming based at least in part upon the identifying information read from the disposable by the infusion pump; and
    the infusion pump delivering infusate sufficient to prime the disposable, based upon the self-programming.

7. A method for managing use of a disposable with an infusion pump, comprising:
    adding validity information about a particular set of disposables to a list of disposables;
    an infusion pump reading identifying information from a disposable that is one of the particular set of disposables;
    determining that the disposable is not valid for use, based at least in part upon comparison of the identifying information read from the disposable by the infusion pump with the validity information about the particular set of disposables on the list of disposables;
    the infusion pump notifying a user that the disposable has been determined to be not valid for use;
    allowing the user to override a determination to not deliver an infusate and specify use of the disposable despite the determination that the disposable is not valid for use without changing the validity information; and
    the infusion pump delivering the infusate if the user specifies use of the disposable, without changing the validity information.

8. The method of claim 7, further comprising modifying the validity information about the particular set of disposables on the list of disposables, subsequent to adding the validity information.

9. The method of claim 7, wherein notifying the user that the disposable has been determined to be not valid for use includes notifying the user of a specific reason that the disposable has been determined to be not valid for use.

10. The method of claim 7, further comprising the infusion pump modifying at least one operating parameter based at least in part the identifying information read from the disposable by the infusion pump.

11. The method of claim 10, wherein the at least one operating parameters relates to occlusion detection.

12. The method of claim 7, further comprising:
    the infusion pump self-programming to deliver infusate sufficient to prime the disposable, the self-programming based at least in part upon the identifying information read from the disposable by the infusion pump; and the infusion pump delivering infusate sufficient to prime the disposable, based upon the self-programming.

13. A method for managing use of a disposable with an infusion pump, comprising:
an infusion pump obtaining identifying information about an attached disposable;
the infusion pump self-programming to deliver infusate sufficient to prime the disposable, the self-programming based at least in part upon the identifying information;
the infusion pump delivering infusate sufficient to prime the disposable prior to delivering infusate, based upon the self-programming.

14. The method of claim 13, wherein the obtaining identifying information includes receiving user input via a user interface of the infusion pump.

15. The method of claim 13, wherein the obtaining identifying information includes a reader of the infusion pump reading a tag of the disposable.

16. A method for managing use of a plurality of disposables with a corresponding plurality of infusion pumps, comprising:
each of the plurality of infusion pumps obtaining identifying information about an attached disposable;
providing an infusion planning system for coordination of medical care including management of the plurality of infusion pumps;
inputting identifying information, of the disposables being used for planned therapies for several patients concurrently including information about the model of the disposable, to the infusion planning system;
transmitting such identifying information to a pharmacy for demand planning and physician order forecasting as changes in previously planned patient therapies occur; and,
requiring a user to override a determination to not deliver in every case that a disposable is determined not to be valid for use, if the disposable is to be used despite the determination that the disposable is not valid for use.

17. A method for managing use of a plurality of disposables with a corresponding plurality of infusion pumps, comprising:
each of the plurality of infusion pumps obtaining identifying information about an attached disposable;
providing an infusion planning system for coordination of medical care including management of the plurality of infusion pumps;
inputting identifying information, of the disposables being used for planned therapies for several patients concurrently including information about the model of the disposable, to the infusion planning system;
transmitting such identifying information to a pharmacy for demand planning and physician order forecasting as changes in previously planned patient therapies occur; and
enabling the user to enter a blanket override to always use a disposable regardless of whether or not they have been determined to be valid for use.

18. A method for managing use of a disposable with an infusion pump, the infusion pump adapted for delivering a variety of infusate types, comprising:
adding validity information about a particular set of disposables to a list of disposables, the disposables adapted for detachable fluidically coupling with the pump;
modifying the validity information about the particular set of disposables on the list of disposables, subsequent to adding the validity information;
an infusion pump reading identifying information from a disposable, the identifying information including infusate information about an infusate contained within the disposable, the infusate information including an infusate type from the variety of infusate types, the infusion pump comprising an ambulatory drug delivery pump having a control module and a reservoir cassette comprising the disposable, wherein the reservoir cassette is detachably couplable to said control module, the identifying information being conveyed from the reservoir cassette to the control module upon coupling of the reservoir cassette to the control module;
determining whether the disposable is valid for use, based at least in part upon comparison of the identifying information read from the disposable by the infusion pump with the validity information about the particular set of disposables on the list of disposables; the infusion pump making a determination of whether to deliver or not deliver the infusate based at least in part upon the determining whether the disposable is valid for use;
the infusion pump self-programming to deliver infusate sufficient to prime the disposable, the self-programming based at least in part upon the identifying information read from the disposable by the infusion pump; and
the infusion pump delivering infusate sufficient to prime the disposable, based upon the self-programming.

19. The method of claim 18, further comprising the infusion pump modifying at least one operating parameter based at least in part the identifying information read from the disposable by the infusion pump.

* * * * *